United States Patent [19]

Drewlow

[11] Patent Number: Plant 7,286

[45] Date of Patent: Jul. 31, 1990

[54] KALANCHOE PLANT NAMED PASSIONATE

[75] Inventor: Lyndon W. Drewlow, Ashtabula, Ohio

[73] Assignee: Mikkelsens, Inc., Ashtabula, Ohio

[21] Appl. No.: 318,056

[22] Filed: Mar. 2, 1989

[51] Int. Cl.[5] ..... A01H 5/00

[52] U.S. Cl. ..... Plt./68

[58] Field of Search ..... Plt./68

[56] References Cited

U.S. PATENT DOCUMENTS

P.P. 5,876 2/1987 Mikkelsen ..... Plt. 68

*Primary Examiner*—Howard J. Locker

*Attorney, Agent, or Firm*—Foley & Lardner, Schwartz, Jeffery, Schwaab, Mack, Blumenthal & Evans

[57] ABSTRACT

A Kalanchoe plant named Passionate specifically developed for its ability to produce cut flowers. In addition, Passionate has upright and tall growth, excellent lateral branching, small lavender pink flowers, floriferous habit, and long lasting flowers which remain open under low light conditions.

1 Drawing Sheet

The present invention relates to a new and distinctive cultivar of Kalanchoe plant, botanically known as *Kalanchoe blossfeldiana,* and known by the cultivar name Passionate. The new cultivar was developed by me through controlled breeding by crossing Eternity (U.S. Pat. No. P.P. 5,253) (see parent) with Acapulco (unpatented) (pollen parent). The principal objective of the breeding program was to develop new Kalanchoe cultivars having certain desired characteristics and which could be used to produce cut flowers.

Asexual reproduction of stem cuttings has shown that the unique features of this new Kalanchoe are stabilized and are reproduced true to type in successive propagations.

The following characteristics distinguish the new Kalanchoe from both its parent cultivars and other cultivated Kalanchoes of this type known and used in the floriculture industry. In order to describe the characteristics more meaningfully, references are made to known pot type Kalanchoe cultivars, including Eternity (U.S. Pat. No. P.P. 5,253), Dignity (U.S. Pat. No. P.P. 5,255), Bingo (U.S. Pat. No. P.P. 5,876) and Sensation (U.S. Pat. No. P.P. 4,727). Also referred to are Desert Blaze, Sombrero, Lemon Drop and Bashful, all cut flower type Kalanchoe cultivars of applicant disclosed in pending patent applications.

1. Passionate is an upright cut flower type Kalanchoe characterized by lavender pink flowers which are deeper in color than Dignity (a light lavender pink), Eternity (a salmon organe), Bindo (a brighter pink), and Sensation (a deep lavender rose). All of the comparison cultivars are pot type in growth.

2. Passionate is much taller (43–47 cm) than the four pot type Kalanchoes (18–22 cm tall when grown without grown regulators), similar in height to Sombrero (43–47 cm), but is slightly shorter than Desert Blaze (40–52 cm), Lemon Drop (53–57 cm), and Bashful (48–52 cm).

3. Passionate generally has ten lateral branches similar to Bashful, Sombrero and Eternity, while Lemon Drop, Desert Blaze, Sensation and Bingo generally have eight lateral branches.

4. Passionate is the only cut flower type of this group that displays secondary branching of the lower lateral branches. This characteristic also occurs in the pot types Eternity and Sensation, but not Bingo.

5. Flowers of Passionate are smaller (14 mm) than any of the comparison cultivars but are so numerous that the overall effect is a mass of color.

6. Leaves of Passionate are larger than Bashful, similar in size to Eternity, and smaller than all the other comparison cultivars.

7. Leaf color of Eternity and Bashful are darker green than Passionate, with Lemon Drop and Sombrero having lighter green leaves and the other comparison cultivars being similar in leaf color.

8. Leaf margins in Passionate are finely lobed and deep cut like Desert Blaze, Bashful, Eternity and Bingo, while Sensation, Dignity, Lemon Drop and Sombrero are larger lobed and shallower cut.

9. Mature stigmatic surface of Passionate has a reddish pink tint as does Desert Blaze, Bashful and Sensation, while the rest of the comparison cultivars are only whitish in color.

10. The five cut flower type Kalanchoes tend to have very little basal branching from the lower two nodes while the four pot plant types have much more basal branching.

11. The inflorescence of Passionate and the other four cut flower types are open with flowers carried at the end of long strong branches, while the pot types have a dense compact inflorescence with flowers carried at the end of short branches.

12. Long lasting lavender pink flowers.

13. Strong, upright branches.

14. Flowers remain open under low light conditions after one dark to light conditioning cycle after cutting.

15. Can be grown on a schedule to provide cut flowers every week of the year.

The accompanying colored photograph is a top perspective view illustrating the overall appearance of Passionate, with colors being as true as reasonably possible to obtain in a colored reproduction of this type. The photograph was taken in late June 1988.

The following is a detailed description of my new Kalanchoe culitvar based on plants produced under commercial practices in Ashtabula, Ohio, under greenhouse conditions. Color references are made to The Royal Horticultural Society Colour Chart except where general color terms of ordinary dictionary significance are used.

The description is based on plant cuttings five (5) weeks old stuck in six (6) inch pots and given two (2) weeks of long day and then short days to induce flowering. The plants were grown at 64°-68° F. night temperatures. Measurements were taken twelve (12) weeks after the start of short days, with plant height being measured from the soil line of the plant.

Parentage: A controlled cross between Eternity (female parent) and Acapulco (male parent).

Propagation:

(*A*) *Type cutting.*—Stem tip cutting up to 3 cm long.

(*B*) *Time to root.*—10 days at 21° C. summer; 14 days at 21° C. winter.

(*C*) *Rooting habit.*—Abundant, fine, fibrous roots.

Plant description:

(*A*) *Form.*—Tall, upright, with flower clusters (inflorescence) carried well above leaf mass on long stems; larger leaves in the lower part of the plant and smaller leaves up in the flower cluster.

(*B*) *Habit of growth.*—Upright, vigorous; branching occurs from the upper nodes with only an occasional lateral from the basal node. Flower cluster is a spray form. Environment will play a role in how tall a plant will get.

(*C*) *Foilage.*—Leaves simple and opposite. (1) Size: Average; full grown leave on a plant grown in a 15 cm pot are 10 to 11 cm long and 5.5 to 6.0 cm wide. (2) Shape: Ovate; apex obtuse; base rounded. (3) Texture: Glabrous, coriaceuos and succulent. (4) Margin: Crenate, some very deeply lobed. (5) Color: Young foilage, top side 146A; Young foilage, under side 146C; Mature foilage, top side 147A; Mature foilage, under side 147B.

Flowering description:

(*A*) *Flowering habits.*—Inflorescence is a cyme. Terminal flower on main axis opens first followed by the terminal flowers of the side branches, continuing with the subsequent development of branches in the inflorescence. Inflorescence is made up of the main stem and up to ten lateral branches, with some of the lower lateral branches branching again. The inflorescence is 33-36 cm in height and 14-18 cm in diameter, and is open.

(*B*) *Natural flowering season.*—Early January. Flowering time under controlled daylength at 20° C. in summer is nine weeks; in winter is twelve weeks. Flowering time depends on temperature, light intensity and other growing conditions. In general, higher temperatures (to the point of heat delay) and increased light intensity will speed up flowering, and low temperatures and light intensity will delay flowering. Other conditions that can cause delay in the flowering are low fertility, very high night temperatures (80° F. plus) and moisture stress.

(*C*) *Flower buds.*—Oblong, up to 8 mm long just before showing first color, developing tubular as flower petals mature. Sheathed with four green sepals.

(*D*) *Flowers borne.*—Compound dichasial cymes, primary peduncle 5 mm in diameter just below the first branch of the influorescence; length will vary depending on growing conditions. In general, puduncles will be shorter when plants are moisture stressed, grown well spaced, grown under high light intensity, grown under low temperatures, or are given applications of growth regulators. If plants are grown crowded and/or under low light conditions, the peduncles will tend to stretch badly. Pedicels vary in length depending on where they are located in the inforescence. The pedicels become shorter the higher they are in the inflorescence, that is, the closer they are to the apical meristem.

(*E*) *Quantity of flowers.*—Highly floriferous, with the main stem and up to ten lateral branches having 50 or more flowers each.

(*F*) *Petals.*—(1) Shape: Almost rounded, top cuspidate. (2) Color: Top side when opening 67C, fading first to 68B, then to 81D and then to 75A-B. In view of numerous changes in color, precise values are difficult; under side approximately 68C. (3) Number of Petals: 4. (4) Size: 7 mm long, 5 mm wide; total flower diameter 14 mm.

(*G*) *Reproductive organs.*—(1) Number of Stamens: Eight. (a) Anther shape: Flat elliptical; color—yellowish-green. (b) Filament color: Light green. (c) Pollen color: Yellow. (2) Pistils: (a) Stigma shape: Flat; color—greenish yellow with pink at center. (b) Style color: Yellowish green. (c) Ovaries: Number—4; size—6 mm; color—green.

Disease resistance: Passionate has shown resistance to powdery mildew. No other disease problems to date.

I claim:

1. A new and distinct cultivar of Kalanchoe plant named Passionate, as illustrated and described.

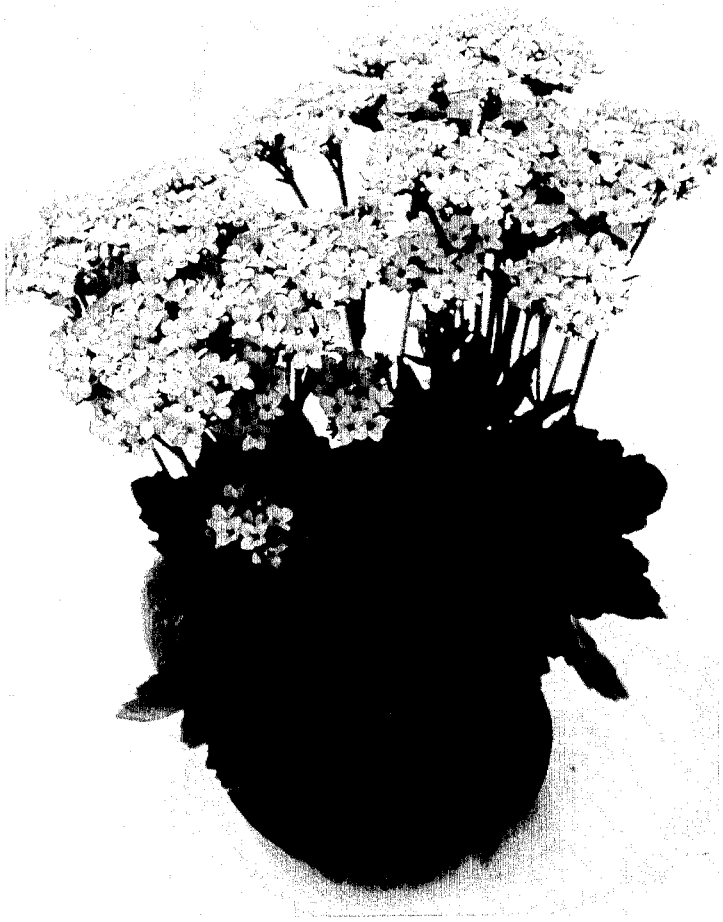

* * * * *